(12) United States Patent
Heske

(10) Patent No.: US 12,414,836 B2
(45) Date of Patent: Sep. 16, 2025

(54) IMPLANTABLE MARKER

(71) Applicant: BIP BIOMED, INSTRUMENTE & PRODUKTE GMBH, Türkenfeld (DE)

(72) Inventor: Thomas Heske, Grafrath (DE)

(73) Assignee: BIP BIOMED, INSTRUMENTE & PRODUKTE GMBH, Türkenfeld (DE)

( * ) Notice: Subject to any disclaimer, the term of this patent is extended or adjusted under 35 U.S.C. 154(b) by 380 days.

(21) Appl. No.: 17/629,429

(22) PCT Filed: Jul. 21, 2020

(86) PCT No.: PCT/EP2020/070548
§ 371 (c)(1),
(2) Date: Jan. 24, 2022

(87) PCT Pub. No.: WO2021/013831
PCT Pub. Date: Jan. 28, 2021

(65) Prior Publication Data
US 2022/0241048 A1    Aug. 4, 2022

(30) Foreign Application Priority Data
Jul. 24, 2019  (DE) .................. 10 2019 210 963.2

(51) Int. Cl.
*A61B 90/00*    (2016.01)

(52) U.S. Cl.
CPC ...... *A61B 90/39* (2016.02); *A61B 2090/3912* (2016.02); *A61B 2090/3925* (2016.02); *A61B 2503/40* (2013.01)

(58) Field of Classification Search
CPC .............. A61B 90/39; A61B 2090/3904–3995
See application file for complete search history.

(56) References Cited

U.S. PATENT DOCUMENTS 4,041,931 A * 8/1977 Elliott ................. A61B 17/11
                                                24/549
5,489,295 A * 2/1996 Piplani ................ A61F 2/958
                                                623/1.34
(Continued)

FOREIGN PATENT DOCUMENTS

EP    1105053 A1    6/2001
EP    1871266 B1    3/2015
(Continued)

OTHER PUBLICATIONS

Anonymous, "Kugelschreiber-Wikipedia"; https://de.wikipedia.org/w/index.php?title=Kugelschreiber&oldid=190392853. XP055742811; Jul. 13, 2019, 13 pages.
(Continued)

*Primary Examiner* — Anh Tuan T Nguyen
*Assistant Examiner* — Younhee Choi
(74) *Attorney, Agent, or Firm* — Fitch, Even, Tabin & Flannery LLP

(57) ABSTRACT

An implantable marker for marking an intracorporeal tissue region of an animal or human, including at least one strand produced from biocompatible material and which has a three-dimensional shape impressed during a shaping process. The strand adopts the three-dimensional shape after cessation of an external mechanical constraint that forced the strand to adopt a compacted three-dimensional shape. The three-dimensional shape impressed upon the strand comprises at least two fixed strand eyelets with each eyelet being formed by at least one helical winding of the strand and having at least one of shape and relative spatial position being different in the compacted three-dimensional shape forced upon them by the external mechanical constraint and the three-dimensional shape adopted after cessation of the mechanical constraint.

21 Claims, 3 Drawing Sheets

(56) References Cited

U.S. PATENT DOCUMENTS

| | | | | |
|---|---|---|---|---|
| 5,669,936 | A | * | 9/1997 | Lazarus ................ A61M 25/10 |
| | | | | 623/1.23 |
| 5,824,044 | A | * | 10/1998 | Quiachon ............... A61F 2/954 |
| | | | | 623/1.23 |
| 6,053,925 | A | | 4/2000 | Barnhart |
| 6,136,015 | A | * | 10/2000 | Kurz ................ A61B 17/12113 |
| | | | | 606/191 |
| 10,226,321 | B2 | * | 3/2019 | Shinar ...................... A61F 2/01 |
| 2001/0023322 | A1 | | 9/2001 | Espositio et al. |
| 2005/0059888 | A1 | | 3/2005 | Sirimanne et al. |
| 2007/0191884 | A1 | * | 8/2007 | Eskridge .......... A61B 17/12113 |
| | | | | 606/213 |
| 2014/0221828 | A1 | | 8/2014 | Mckinnis et al. |
| 2015/0272542 | A1 | * | 10/2015 | Shuman ................ A61B 90/39 |
| | | | | 600/424 |

FOREIGN PATENT DOCUMENTS

| | | | |
|---|---|---|---|
| WO | 9943268 | A1 | 9/1999 |
| WO | 2007094001 | A2 | 8/2007 |

OTHER PUBLICATIONS

European Patent Office; European office action in corresponding European Patent Application No. 20 747 352.1, dated Sep. 7, 2023; 7 pages.

\* cited by examiner

IMPLANTABLE MARKER

CROSS-REFERENCE TO RELATED APPLICATIONS

This application claims priority from International Patent Application No. PCT/EP2020/070548 filed Jul. 21, 2020, which claims priority from German Application No. 10 2019 210 963.2 filed Jul. 24, 2019, which are hereby incorporated herein by reference in their entirety.

BACKGROUND OF THE INVENTION

Field of the Invention

The invention relates to an implantable marker for marking an intracorporeal tissue region of an animal or human. The implantable marker has at least one strand which is produced from biocompatible material and which has a three-dimensional shape impressed upon it in the course of a shaping process. The strand adopts this three-dimensional shape after cessation of an external mechanical constraint that forced the strand to adopt a compacted three-dimensional shape.

Description of the Prior Art

Generic implantable markers are used to identify tumours in human or animal soft tissue. For example, after a breast biopsy, a marker is often inserted by means of a cannula at the site of tissue removal and, after reaching the desired location, is ejected distally from the cannula by use of a stylet. The marker placed intracorporally remains stationary and offers a doctor the possibility of locating an area of tissue at least one of to be treated and diagnosed with the aid of an imaging procedure, preferably using ultrasound images, and of then observing it over the long term.

For this purpose, a tissue marker for human tissue can be found in U.S. Pat. No. 6,053,925, which has two wires produced from shape-memory metal twisted together. The marker, which is to be placed in a tissue area that is to be marked in a manner that is as invariable as possible, has a ring or coil-shaped form.

US published patent application 2005/0059888 A1 describes a marker that marks the location of an intracorporeally placed biological absorber body. The marker material is detectable by mammography, radiology and ultrasound, for example a wire attached to the absorber body.

US published patent application 2001/0023322 A1 describes a cannula-like positioning unit for an intracorporeally insertable marker. The marker is a shape-memory metal wire which, after intracorporeal positioning, deforms at least at the tip of the wire into a ring or coil for the purpose of fixed positioning in an area of tissue to be marked.

Lastly, a generic marker for human or animal tissue can be found in document EP 1 871 266 B1, which is made of a pre-programmable material, preferably a nickel-titanium alloy, in the form of a ring, which, after a longitudinal extension is forced on the material, reverts to the pre-programmed ring shape after release.

All known generic markers, for example in particular the ring-shaped markers explained above, are ultrasound reflectors due to their material properties, but the known markers stand out to different degrees on the basis of the ultrasound images depending on the direction of sonication along which the ultrasound waves interact with the marker. If a mostly fan-shaped propagating ultrasonic wave field impinges on a previously described ring marker, the ring plane is oriented orthogonally to the fan plane of the propagating ultrasonic waves, then only two point-like ultrasonic reflection signals are distinguished, which reproduces the ring contour when the ultrasonic field is tilted relative to the ring-shaped marker. If, by contrast, the fan-shaped ultrasonic wave field is oriented parallel to the ring plane, possible reflection signals on the ultrasonic image form a line with a length corresponding to the diameter of the ring marker.

A great deal of experience is thus required to clearly recognize such known markers, which have dimensions in the range of a few millimeters, spatially and in a spatially resolved manner within the biological tissue environment.

SUMMARY OF THE INVENTION

The invention is an implantable marker for marking an intracorporeal tissue region of an animal or human. The implantable marker has at least one strand which is produced from biocompatible material and which has a three-dimensional shape impressed upon it in the course of a shaping process. The strand adopts this three-dimensional shape, after cessation of an external mechanical constraint that forced the strand to adopt a compacted three-dimensional shape, in such a way that the visibility of the implanted marker for a physician during an ultrasound examination is significantly improved. In particular, the marker is characterized by a largely isotropic high ultrasound reflectivity independent of the directions to be irradiated with the ultrasound head, so that a visually unambiguous and easy location of the marker is provided to the physician with the aid of an ultrasound-based imaging method.

According to the invention, the implantable marker has features having the three-dimensional shape impressed upon the strand comprising at least two fixed strand eyelets. Each eyelet is formed by at least one helical winding of the strand and at least one shape and relative spatial position is different in the compacted three-dimensional shape forced upon them by the external mechanical constraint and in the three-dimensional shape adopted after cessation of the mechanical constraint.

The term "fixed strand eyelet" is borrowed from knotology and represents a simple geometric shape characterized by the formation of a circle along the strand. Here, the strand is helically wound at least once and has a helical pitch where the strand touches in an overlapping area of the winding. In contrast to a closed ring shape, a fixed eyelet does not appear as a straight line with constant line thickness when exposed to lateral ultrasonic waves. Instead the fixed eyelet appears as a wedge or double wedge shape having a maximum wedge width corresponding to twice the strand width in the case of a single helical winding. Correspondingly, an ultrasonic signal is formed more clearly with lateral sonication of a fixed strand eyelet composed of a plurality of helical windings.

The implantable marker according to the invention has at least two and preferably three or more, strand eyelets formed along the strand in each case by a helical winding of the strand. Not necessarily, but advantageously, the at least two fixed strand eyelets have identical shapes and dimensions. Of course, eyelet shapes deviating from the circular shape, such as oval or elliptical fixed eyelets, are also conceivable. The shapes and dimensions of the strand eyelets arranged along the strand can also differ from each other. In addition, the spatial position and allocation of the fixed strand eyelets can be uniformly or individually selected by their distance from each other and the orientation of the planes that can be allocated to the fixed strand eyelets.

Metal shape-memory material is particularly suitable for the manufacture of the strand and the impressing of the three-dimensional shape according to the invention along the strand, which preferably has a pseudoelastic behavior, so that the wire having the shape-memory material returns to its three-dimensional shape which is impressed by a high-temperature process, in a shape-retaining manner, even if the wire is strongly elastically deformed under the application of external force. Particularly suitable materials are nickel-titanium ("Nitinol"), nickel-titanium-copper, copper-zinc, copper-zinc-aluminum or copper-aluminum-nickel.

In one possible embodiment of the implantable marker according to the invention, the strand comprises two fixed strand eyelets which are integrally connected to each other via a strand portion. For the purpose of intracorporeal location, the strand is converted by an external mechanical constraint into a compacted three-dimensional shape in which the at least one helical winding of the strand eyelets is completely stretched by tensile forces acting along the strand so that the windings are largely completely elastically deformed to form a linear strand. In this compacted form, the strand is introduced into a hollow cannula through which the strand can be placed intracorporeally.

The strand is ejected in a manner known per se with the aid of a stylet. As soon as the strand in the compacted three-dimensional shape is ejected distally from the hollow cannula, the strand spontaneously assumes its impressed three-dimensional shape and spontaneously forms the at least two fixed strand eyelets. Depending on the impressed three-dimensional shape, the strand eyelets can each span a common eyelet plane. Preferably, the individual fixed strand eyelets can be oriented along the strand with different eyelet planes, to be along the strand portion that integrally connects the two fixed strand eyelets with each other, a torsional, material-inherent material tension is impressed, which orients the two fixed strand eyelets twisted relative to each other.

Alternatively or in combination with the above twisting of both fixed strand eyelets integrally connected to each other via a strand portion, a further exemplary embodiment provides for tilting or pivoting of both fixed strand eyelets by a locally impressed curvature along the strand portion integrally connecting both fixed strand eyelets to each other.

In a further exemplary embodiment, the at least two fixed strand eyelets are integrally connected via a strand portion so that they are arranged in the compacted three-dimensional shape imposed by the external mechanical constraint without overlapping next to each other along a virtual linear axis. In this state, they are inserted into a hollow cannula dimensioned correspondingly to the eyelet diameter and, as already explained in the previous case, are implanted distally via the hollow cannula inside a body with the aid of a stylet. Immediately after exiting the hollow cannula, a spontaneous elastic deformation of the implantable marker into its impressed three-dimensional shape takes place. In the case of two fixed strand eyelets that are integrally connected to each other via a strand portion, these can individually assume at least one of their initially impressed shape and size as well as their spatial position in relation to each other.

In another preferred embodiment, at least three fixed strand eyelets are formed along the strand, which are arranged in series along a virtual linear axis in the compacted three-dimensional shape imposed by the external mechanical constraint. In this compacted three-dimensional shape, the implantable marker can be placed intracorporeally through a suitably dimensioned hollow cannula. As soon as the mechanical force exerted on the marker by the hollow cannula is removed by distal ejection, the implantable marker assumes its initially impressed three-dimensional shape, which differs significantly from the arrangement in series of the at least three fixed strand eyelets along the virtual linear axis.

The following figuratively presented exemplary embodiments illustrate the wide range of possible designs of the implantable marker according to the invention with the three-dimensional shapes impressed on it in accordance with the invention. The implantable marker is characterized by improved visibility from all spatial directions with the aid of an ultrasound-based imaging process.

In addition to the impressed three-dimensional shape of the implantable marker, which is the reason for the improved ultrasonic wave-based detectability, a surface structuring, which is preferably applied or incorporated along the strand surface, also contributes to increasing the ultrasonic wave reflectivity, which is preferably characterized in the form of a surface roughening or a stochastic or at least one of a regular arrangement of groove-like, groove-shaped and notch-like recesses on the strand surface.

As an alternative to forming the implantable marker according to the invention in the form of a wire having metal shape-memory material and its three-dimensional shape impressed in accordance with the invention, it is also possible to manufacture the strand from a suitably selected alternative biocompatible material that has the same or similar shape-memory properties. For example, shape-memory polymers or composite materials that combine polymers with shape-memory alloys are suitable for this purpose.

BRIEF DESCRIPTION OF THE DRAWINGS

Without limiting the general idea of the invention, the invention is described below by way of exemplary embodiments with reference to the drawing. The figures show.

DETAILED DESCRIPTION OF THE INVENTION

Figure 1:
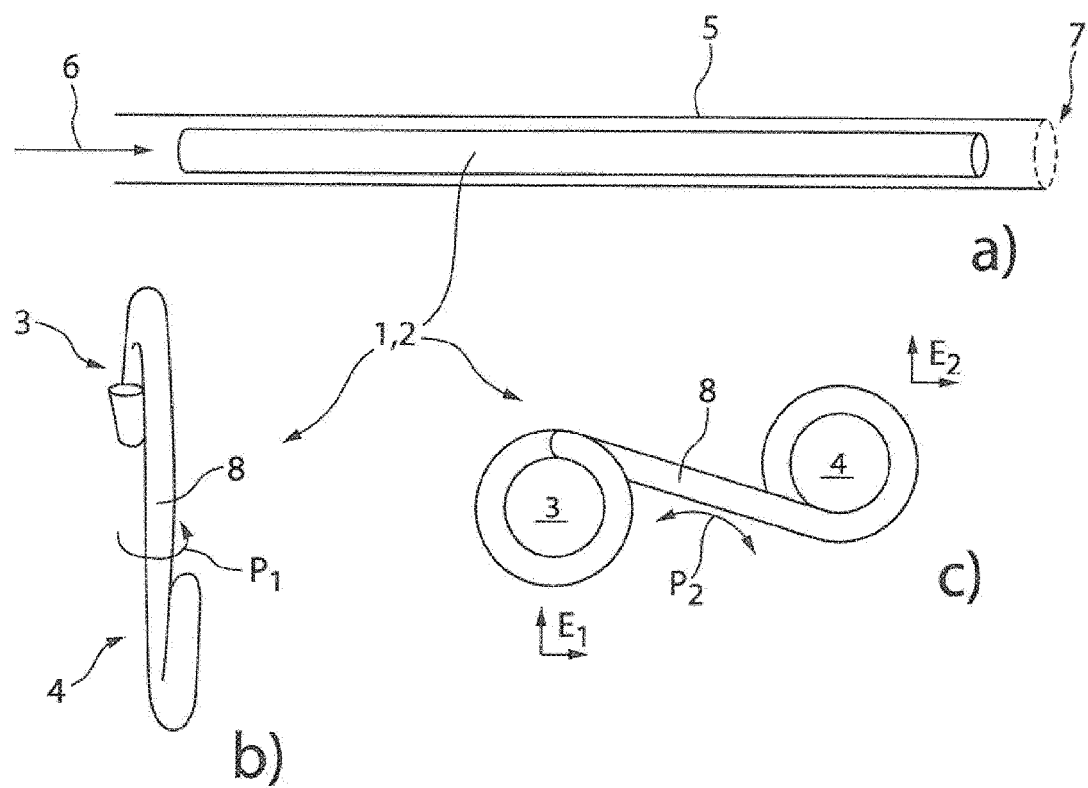
FIG. 1a is a first embodiment of an implantable marker formed in accordance with the invention in a compacted three-dimensional shape.
FIG. 1b, and c show a plan and a side view of the implantable marker according to FIG. 1a with an impressed three-dimensional shape.

FIGS. 1a-c illustrate a first exemplary embodiment of an implantable marker formed in accordance with the invention. FIGS. 1b and c show the marker 1 in plan and side views, in each case in its three-dimensionally impressed three-dimensional shape. The marker 1 is produced from a round wire 2, preferably made of nitinol (NiTi), and has two fixed strand or wire eyelets 3, 4 in its impressed three-dimensional shape. The wire eyelets 3, 4 are each produced by a single-layer helical winding along the wire made of nitinol. The winding direction of both wire eyelets 3, 4 is oriented in opposite directions.

For the purpose of intracorporeal location of the implantable marker 1, the marker 1 is transferred by an external mechanical constraint into the linearly stretched, compacted three-dimensional shape illustrated in FIG. 1a. For this purpose, the nitinol wire 2 is stretched under tensile force in the longitudinal direction of the wire from its impressed three-dimensional shape illustrated in FIGS. 1b and c and is inserted into a hollow cannula 5.

With the help of a stylet 6, the wire 2 in the compacted three-dimensional shape is pushed through the distal opening 7 of the hollow cannula 5. Immediately after the marker 1 has emerged through the distal opening 7 of the hollow cannula 5, the marker 1 assumes the impressed three-dimensional shape illustrated in FIGS. 1b and c. The two fixed wire eyelets 3, 4, which are integrally connected to each other by a wire portion 8, each have eyelet planes E1, E2 lying in the drawing plane. Of course, the eyelet planes E1, E2 associated with the fixed wire eyelets 3, 4 can also be inclined or rotated in relation to each other. For this purpose, a corresponding mechanical material-inherent pre-tension must be provided along the wire portion 8, by use of which pre-tension a twisting of both fixed wire eyelets 3, 4 relative to each other is initiated, which is represented in this respect by the arrow P1 illustrated in FIG. 1b. Alternatively to the above twisting or in combination with the twisting, a mechanically pre-programmed wire curvature can be introduced along the wire portion 8, which is straight in FIGS. 1b, c, as indicated by the arrow P2 which is in FIG. 1c.

The three-dimensional shape impressed on the implantable marker 1, shown in FIG. 1, enables easy and reliable detection with the aid of an ultrasound-based imaging method, regardless of the spatial orientation of the implanted marker 1 relative to the intracorporeal ultrasound wave field.

Figure 2:
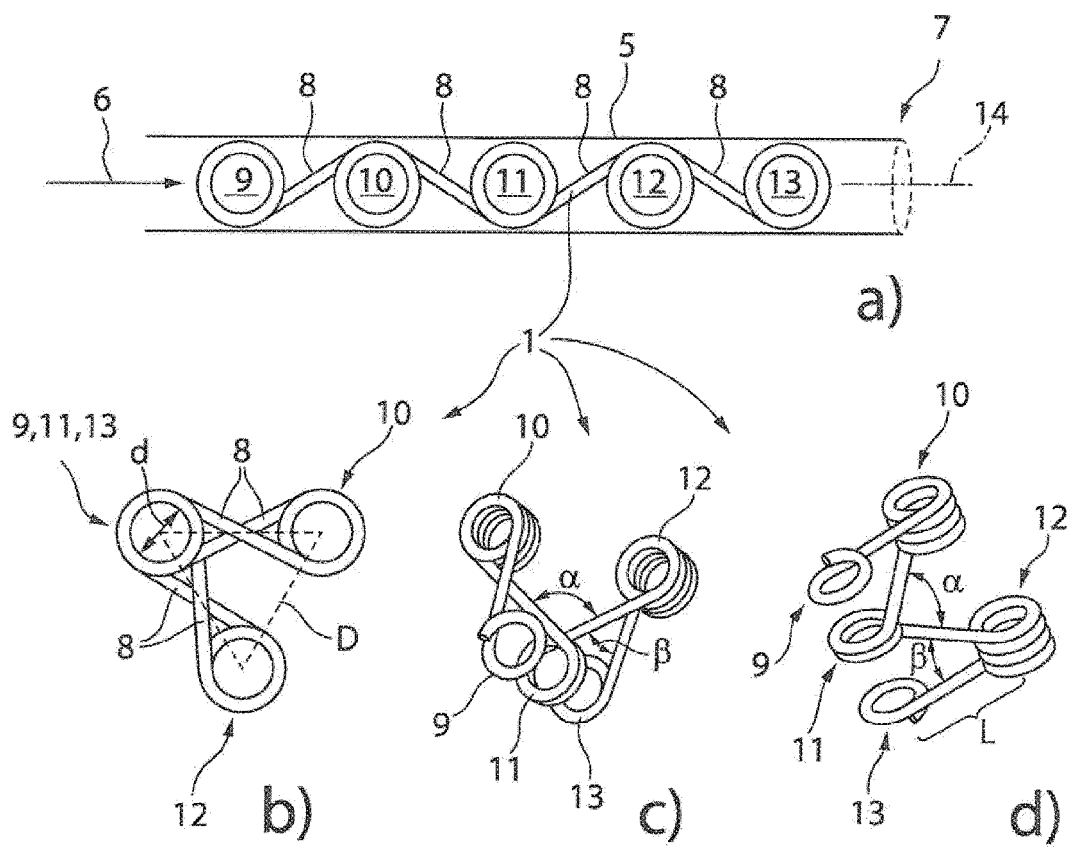
FIG. 2a shows a second exemplary embodiment of an implantable marker in a compacted three-dimensional shape.
FIG. 2b, c, and d show different viewing angles on the implantable marker according to FIG. 2a in the impressed three-dimensional shape.

FIGS. 2a-d illustrate a preferred advanced embodiment for forming an implantable marker 1 according to the invention having an impressed three-dimensional shape shown from different viewing angles in FIGS. 2b-d.

In this case, the implantable marker 1 has five fixed strand or wire eyelets 9-13, each of which is produced integrally, preferably from a nitinol wire 2. From FIGS. 2b-d, which show the implantable marker 1 at different perspective viewing angles, it can be seen that the fixed wire eyelets 10 and 12 each provide more than one helical winding. The number of windings from which a fixed wire eyelet is made can be variably selected as desired. Also, the number of wire eyelets along the wire 2 as well as their distances and orientations to each other can be chosen arbitrarily.

FIG. 2a shows the compacted three-dimensional shape of the implantable marker 1, in which the fixed wire eyelets 9 to 13 are arranged linearly along a virtual linear axis 14 under external mechanical tensile constraint, so that they can be inserted inside a hollow cannula 5. As soon as the marker 1 in the compacted three-dimensional shape has been pushed distally out of the hollow cannula 5 with the aid of the stylet 6, the marker 1 abruptly, that is spontaneously, assumes the impressed three-dimensional shape illustrated in FIGS. 2b-d. The fixed wire eyelets 9-13 form a virtual linear axis 14 under external mechanical traction. In this case, the fixed wire eyelets 9-13 together with the wire portions 8 form a three-dimensionally determined structure or three-dimensional shape which, in interaction with an ultrasonic wave field, generates significant reflection signals which appear visually significant on an ultrasonic image. In addition, due to the abrupt transition from the compacted three-dimensional shape shown in FIG. 2a to the impressed three-dimensional shape illustrated in FIGS. 2b-d, the implantable marker 1 formed in accordance with the invention is able to enter into a close and mechanically stable connection with the biological tissue surrounding the marker 1, so that undesired migration of the implanted marker 1 within the tissue can be ruled out from the outset.

For the sake of completeness only, it should be noted that, in deviation from the impressed three-dimensional shape of the implantable marker 1 illustrated in FIGS. 2b-d, twists or curvatures may also be introduced along the wire portions 8 and shown in FIGS. 1b, c by the arrow representations P1, P2.

Figure 3:
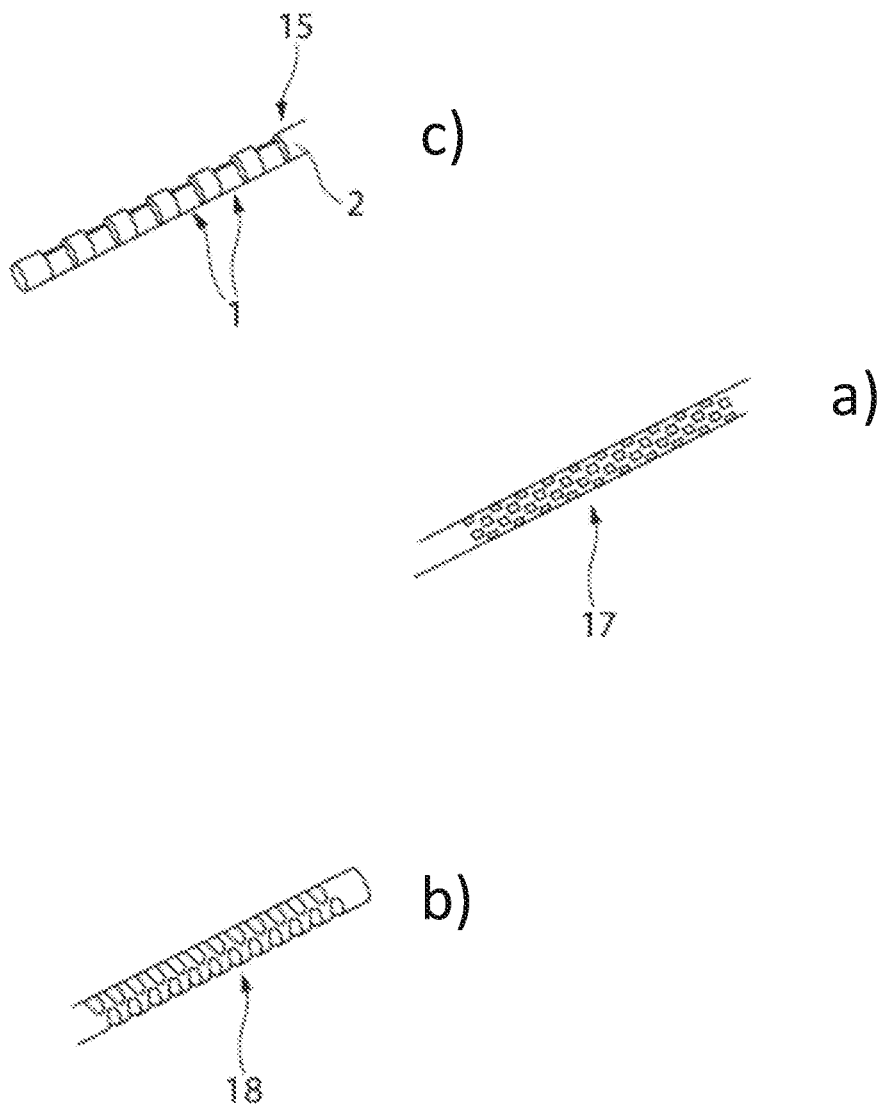
FIGS. 3a-c show different strand surface structures.

In order to improve the ultrasound reflectivity of the implantable marker 1 according to the invention, the surface 15 of the strand or wire 2 can be structured. Possible surface structurings of the strand or wire 2 are illustrated in FIGS. 3a-c. FIG. 3a shows groove-shaped impressions 17 extending along the strand or wire surface 15. In FIG. 3b, the strand surface 15 is provided with a multiplicity of local indentations 18 that provide increased ultrasonic reflectivity. FIG. 3c provides a grooved surface structuring 19 along the strand or wire surface 15.

The individual features of the individual exemplary embodiments may be combined as desired. The lengths of the wire portions 8 in FIGS. 2a to d, each with the same dimensions, can also be individually dimensioned without adversely affecting the ultrasonic wave reflectivity.

The wire eyelets can be seen in the plan view in FIG. 2b, to project into an equilateral triangle D and thus represent a mathematically defined or geometrically determined recognition pattern, which is particularly suitable for autonomous image evaluation.

The following design parameters of the three-dimensional shape impressed into the implant 1 can be selected as desired:
diameter d of the wire eyelets,
length L of the wire portions,
angles α, β between the wire portions 8, as seen in FIGS. 2c, d,
number of helical windings per wire eyelet 9-13,
geometric shape of each wire eyelet: circular, elliptical, oval, with n angles, and
winding direction of the helical windings.

LIST OF REFERENCE SIGNS 1 implantable marker
2 strand or wire
3, 4 fixed eyelet
5 hollow cannula
6 stylet
7 distal opening
8 strand portion, wire portion
9-13 fixed eyelet
14 virtual linear axis
15 strand surface or wire surface
16 groove-shaped impression
17 local indentations
18 grooved surface structure
D equilateral triangle
d diameter of fixed eyelet
L length of strand-wire portion
α, β angle between the wire portions

The invention claimed is:
1. A spatially shaped implantable marker configured for implantation to mark an intracorporeal tissue region of a human or animal when deployed from a hollow cannula into the human or the animal comprising:
- at least five spaced apart spatially shaped fixed strand eyelets which are spaced along a strand of biocompatible material, the strand of biocompatible material including an interior portion containing at least three impressed spaced apart fixed strand eyelets and two distal end portions each respectively containing an impressed fixed strand eyelet containing only a helical loop located at a distal most end of the distal end portion, each fixed strand eyelet including at least two helical windings forming a loop having a helical pitch with two end strands of the at least two helical windings touching in an overlap area;
- when the shaped implantable marker is contained by the hollow cannula during implantation into the patient or animal, the at least five strand eyelets are disposed along a virtual linear axis one behind another without overlapping, the hollow cannula exerting a mechanical constraint on the windings;
- when the shaped implantable marker is deployed from the hollow cannula, the mechanical constraint on the windings is removed so that the strand of biocompatible material assumes a spatial shape different than along the virtual linear axis while within the hollow cannula, and the shaped implantable marker is adapted to be implanted in the human or animal thereby marking the intracorporeal tissue region within the human or animal; and
- wherein the spatial shape of the strand of biocompatible material when implanted comprises a defined angle less than 180 degrees between each adjacent fixed strand eyelets such that when the shaped implantable marker is scanned with an ultrasound source for providing ultrasound reflection, the shaped implantable marker is configured to mark the intracorporeal tissue region independent of a direction of irradiation with ultrasound.

2. The implantable marker according to claim 1, wherein:
a winding direction of each of the at least five spaced apart spatially shaped fixed strand eyelets is different between adjacent two spatially shaped fixed strand eyelets arranged along the strand of biocompatible material.

3. The implantable marker according to claim 2, wherein:
each of the five spaced apart spatially shaped fixed strand eyelets has an opening plane; and
the opening plane of each of the at least five spatially shaped fixed strand eyelets is not oriented parallel to the opening plane of any other adjacent spatially shaped fixed strand eyelets.

4. The implantable marker according to claim 3, wherein:
the strand of biocompatible material comprising the at least five spaced apart spatially shaped fixed strand eyelets reflects ultrasonic waves.

5. The implantable marker according to claim 3, wherein:
the strand of biocompatible material comprises at least one material having shape memory properties.

6. The implantable marker according to claim 3, wherein:
the strand of biocompatible material comprises wire of a metallic shape memory material selected from: NiTi ("Nitinol"), NiTiCu, CuZn, CuZnAl or CuAlNi.

7. The implantable marker according to claim 2, wherein:
the biocompatible material reflects ultrasonic waves.

8. The implantable marker according to claim 2, wherein:
the at least five spaced apart spatially shaped fixed strand eyelets includes surface structure which reflects ultrasonic waves of the ultrasound source.

9. The implantable marker according to claim 2, wherein:
the strand of biocompatible material comprises at least one material having shape memory properties.

10. The implantable marker according to claim 2, wherein:
the strand of biocompatible material comprises wire of a metallic shape memory material selected from: NiTi ("Nitinol"), NiTiCu, CuZn, CuZnAl or CuAlNi.

11. The implantable marker according to claim 1, wherein:
each of the five spaced apart spatially shaped fixed strand eyelets has an opening plane; and
the opening plane of each of the at least five spatially shaped fixed strand eyelets is not oriented parallel to the opening plane of any other adjacent spatially shaped fixed strand eyelets.

12. The implantable marker according to claim 11, wherein:
the biocompatible material reflects ultrasonic waves.

13. The implantable marker according to claim 11, wherein:
the strand of biocompatible material comprising the at least five spaced apart spatially shaped fixed strand eyelets reflects ultrasonic waves.

14. The implantable marker according to claim 11, wherein:
the strand of biocompatible material comprises at least one material having shape memory properties.

15. The implantable marker according to claim 11, wherein:
the strand of biocompatible material comprises wire of a metallic shape memory material selected from: NiTi ("Nitinol"), NiTiCu, CuZn, CuZnAl or CuAlNi.

16. The implantable marker according to claim 1, wherein:
the biocompatible material reflects ultrasonic waves.

17. The implantable marker according to claim 16, wherein:
the strand of biocompatible material comprises at least one material having shape memory properties.

18. The implantable marker according to claim 1, wherein:
the at least five spaced apart spatially shaped fixed strand eyelets includes surface structure which reflects ultrasonic waves of the ultrasound source.

19. The implantable marker according to claim 1, wherein:
the strand of biocompatible material comprises at least one material having shape memory properties.

20. The implantable marker according to claim 1, wherein:
the strand of biocompatible material comprises wire of a metallic shape memory material selected from: NiTi ("Nitinol"), NiTiCu, CuZn, CuZnAl or CuAlNi.

21. A method of using the implantable marker of claim 1 comprising placing the implantable marker within the hollow cannula and then distally ejecting the implantable marker within the human or animal with a stylet to cause the implantable marker to spontaneously assume the spatial shape different than along the virtual linear axis while within the hollow cannula to mark the intracorporeal tissue region of the human or animal.

* * * * *